United States Patent [19]

Takano et al.

[11] 4,252,952
[45] Feb. 24, 1981

[54] 7-(α-SUBSTITUTED GLYCINAMIDO)-3-SUBSTITUTED METHYL-3-CEPHEM-4-CARBOXYLIC ACIDS AND THEIR DERIVATIVES

[75] Inventors: Tadayoshi Takano, Hirakata; Susumu Horibe, Takatsuki, both of Japan

[73] Assignee: Fujisawa Pharmaceutical Co., Ltd., Osaka, Japan

[21] Appl. No.: 53,095

[22] Filed: Jun. 28, 1979

Related U.S. Application Data

[62] Division of Ser. No. 796,663, May 13, 1977, Pat. No. 4,178,445, which is a division of Ser. No. 563,116, Mar. 28, 1975, Pat. No. 4,039,536.

[30] Foreign Application Priority Data

| Mar. 28, 1974 | [JP] | Japan | 49-36080 |
| Apr. 9, 1974 | [JP] | Japan | 49-40577 |
| Apr. 10, 1974 | [JP] | Japan | 49-41130 |
| Apr. 11, 1974 | [JP] | Japan | 49-41515 |
| Apr. 11, 1974 | [JP] | Japan | 49-41516 |
| Apr. 15, 1974 | [JP] | Japan | 49-42568 |

[51] Int. Cl.$^3$ ............................................. C07D 501/36
[52] U.S. Cl. ........................................ 544/26; 544/22; 544/27; 544/29
[58] Field of Search ........................ 544/22, 26, 27, 29

[56] References Cited

U.S. PATENT DOCUMENTS 4,039,536   8/1977   Takano et al. ..................... 424/246

Primary Examiner—Paul M. Coughlan, Jr.
Attorney, Agent, or Firm—Dayton R. Stemple, Jr.

[57] ABSTRACT

This invention is concerned with 7-(α-substituted glycinamido)-3-substituted methyl-3-cephem-4-carboxylic acids, derivatives and non-toxic pharmaceutical salts thereof, which possess antibacterial activity, process for preparation thereof, having the following general formula

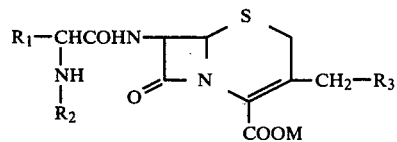

9 Claims, No Drawings

7-(α-SUBSTITUTED GLYCINAMIDO)-3-SUBSTITUTED METHYL-3-CEPHEM-4-CARBOXYLIC ACIDS AND THEIR DERIVATIVES

This is a division, of application Ser. No. 796,663, filed May 13, 1977, now U.S. Pat. No. 4,178,445, which was a division of application Ser. No. 563,116, filed Mar. 28, 1975, now U.S. Pat. No. 4,039,536.

The present invention relates to new cephalosporanic acid derivatives and their preparation. More particularly, it relates to 7-(α-substituted glycinamido)-3-substituted methyl-3-cephem-4-carboxylic acids, their derivatives and their nontoxic pharmaceutically acceptable salts, which possess an antibacterial activity, processes for preparation of the same and a composition thereof.

The cephalosporanic acid derivatives of this invention include compounds represented by the following general formula:

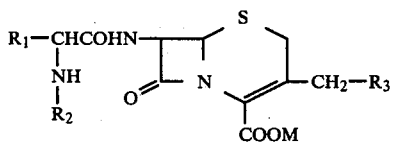

wherein
$R_1$ is hydrogen, lower alkyl, aryl or heterocyclic group, $R_2$ is phenyl(lower)alkanoyl, phenoxy(lower)alkanoyl or phenylthio(lower)alkanoyl, in which the phenyl moiety may be substituted with halogen, nitro, carboxy, sulfo, lower alkyl, lower alkoxy, halo(lower)alkyl or aryloxycarbonyl, $R_3$ is hydrogen, azido, lower alkanoyloxy, aroylthio, in which the aryl moiety may be substituted with one to three lower alkoxy(s), heterocyclic group having quaternary nitrogen atom, heterocyclic-thio group, heterocyclic-carbonylthio group or heterocyclic-thiocarbonylthio group, in which the heterocyclic group (or moiety) may be substituted with lower alkyl, amino(lower)alkyl, in which the amino moiety may have a conventional protecting group or sulfo(lower)alkylamino(lower)alkyl, provided that $R_1$ is hydrogen, lower alkyl or heterocyclic group when $R_2$ is phenoxy(lower)alkanoyl, in which the phenyl moiety have no substituent and $R_3$ is lower alkanoyloxy or lower alkyl substituted heterocyclic-thio group and M is hydrogen, nontoxic pharmaceutically acceptable cation or anionic charge, and their esters.

The term "lower" used in this specification and the claims refers to radicals containing 1 to 6 carbon atom(s).

The term "ester" of the compound [I] may be an lower alkyl ester such as methyl ester, ethyl ester, propyl ester, isopropyl ester, butyl ester, isobutyl ester, pentyl ester, hexyl ester, unsaturated lower alkyl ester such as allyl ester or ethynyl ester, halo(lower) alkyl ester such as 2-iodoethyl ester or 2,2,2-trichloroethyl ester, lower alkanoyloxy(lower)alkyl ester such as acetoxymethyl ester, propionyloxymethyl ester, butyryloxymethyl ester, valeryloxymethyl ester, pivaloyloxymethyl ester, acetoxyethyl ester, propionyloxyethyl ester and the like, trimethylsilyl ester, 2-mesylethyl ester, phenyl(lower)alkyl ester, in which the phenyl moiety may have suitable substituent(s) such as benzyl, 4-methoxybenzyl, 4-nitrobenzyl, phenethyl, trityl, diphenylmethyl, bis(methoxyphenyl)methyl, 3,4-dimethoxybenzyl or 4-hydroxy-3,5-di-tert-butylbenzyl ester, and the like. The lower alkyl esters can, for example, be represented by the formula [I] wherein M is lower alkyl, and the other esters can be also represented in the same manner.

The term "nontoxic pharmaceutically acceptable cation" represented by M includes an alkali metal ion (e.g. sodium ion, potassium ion, etc.,), ammonium ion and an organic quaternary ammonium ion (e.g., triethylammonium, dicyclohexylammonium, diphenylenediammonium, dibenzylethylenediammonium, tetramethylammonium, etc.,) and the like.

The term "lower alkyl" represented by $R_1$ includes methyl, ethyl, propyl, isopropyl, butyl, isobutyl, t-butyl, pentyl, hexyl and the like.

The term "aryl" represented by $R_1$ includes phenyl, tolyl, xylyl, mesityl, cumenyl, naphthyl and the like.

The term "heterocyclic group" represented by $R_1$ is 5 to 6 membered heterocyclic group containing at least one of oxygen, sulfur and nitrogen atoms which, for example, includes a residue of thiophene, pyrrole, pyrazole, imidazole, triazole, thiazole, isothiazole, oxazole, isoxazole, thiadiazole, oxadiazole, tetrazole, pyridine, pyrazine, pyrimidine, pyridazine, pyrrolidine, imidazolidine, piperidine, hexahydropyrimidine, hexahydropyridazine etc., benzene-fused 5 to 6 membered heterocyclic group containing at least one of oxygen, sulfur and nitrogen atoms which, for example, benzothiophene, benzofuran, indole, indazole, benzimidazole, benzothiazole, benzothiadiazole, benzoxazole, quinoline, isoquinoline, phthalazine, quinoxaline, quinazoline, etc., purine, naphthyridine, and the like.

The term "lower alkanoyl" moiety of phenyl(lower)alkanoyl, phenoxy(lower)alkanoyl and phenylthio(lower)alkanoyl for $R_2$, and lower alkanoyloxy for $R_3$ includes formyl, acetyl, propionyl, butyryl, isobutyryl, varelyl, pivaloyl and the like.

The phenyl moiety of phenyl(lower)alkanoyl, phenoxy(lower)alkanoyl or phenylthio(lower)alkanoyl for $R_2$ may have one or more substituent(s) selected from the group consisting of halogen (e.g. chlorine, bromine, iodine), nitro, carboxy, sulfo, lower alkyl (e.g., methyl, ethyl, propyl, isopropyl, butyl, isobutyl, t-butyl, pentyl, hexyl, etc.,), lower alkoxy (e.g., methoxy, ethoxy, propoxy, isopropoxy, butoxy, isobutoxy, t-butoxy, pentyloxy, hexyloxy, etc.,), halo(lower)alkyl (e.g., chloromethyl, bromomethyl, iodomethyl, chloroethyl, 1,2-dichloroethyl, 1,2,-dibromoethyl, trifluoromethyl, etc.,), or aryloxycarbonyl (e.g., phenoxycarbonyl, toly-loxycarbonyl, etc.).

The term "aroylthio" represented by $R_3$ includes benzoylthio, toluoylthio, naphthoylthio and the like, and the aryl moiety may be substituted with one to three lower alkoxy(s) as illustrated above.

The term "heterocyclic-thio group" represented by $R_3$ includes a residue of a thiol compound having a heterocyclic group, in which the heterocyclic moiety may be the same meaning as the heterocyclic group of $R_1$, preferably 5-membered aromatic heterocyclic group containing three or four atoms of oxygen, sulfur and/or nitrogen atoms such as triazole, thiadiazole, oxadiazole, tetrazole and the like, and benzene-fused 5-membered heterocyclic group containing two nitrogen atoms such as benzimidazole, indazole. Said heterocyclic moiety may have one or more substituent(s) selected from the group consisting of lower alkyl (e.g., methyl, ethyl, propyl, isopropyl, butyl, isobutyl, t-butyl, pentyl, hexyl, etc.), amino(lower)alkyl, (e.g., aminomethyl, aminoethyl, aminopropyl, aminobutyl, aminopentyl, etc.,) in which the amino group may have a conventional protecting group, or sulfo(lower)alkylamino(lower)alkyl (e.g., sulfomethylaminomethyl, sulfomethylaminoethyl, sulfoethylaminomethyl, sulfoethylaminoethyl, etc.). And the conventional amino protecting groups are, for example, benzyloxycarbonyl, substituted benzyloxycarbonyl, lower alkoxycarbonyl (e.g., methoxycarbonyl, ethoxycarbonyl, propoxycarbonyl, butoxycarbonyl, t-butoxycarbonyl, etc.), substituted lower alkoxycarbonyl, aryl(lower)alkoxycarbonyl, adamantyloxycarbonyl, trityloxycarbonyl, substituted phenylthio, cycloalkylidene, trifluoroacetyl, halogen substituted lower alkoxycarbonyl, 8-quinolyloxycarbonyl, 2-pyridylmethoxycarbonyl and the like.

The term "heterocyclic-carbonylthio" represented by $R_3$ includes one, in which the heterocyclic moiety may be the same as the heterocyclic group of $R_1$.

The term "heterocyclic-thiocarbonylthio" represented by $R_3$ includes one, in which the heterocyclic moiety may be the same as the heterocyclic group, preferably a nitrogen containing 5 or 6 membered saturated heterocyclic group such as piperidine, pirrolidine, piperazine, hexahydropyrimidine, hexahydropyridazine and the like, and may be substituted with lower alkyl mentioned above.

The term "heterocyclic group having quaternary nitrogen atom" represented by $R_3$ includes six-membered aromatic heterocyclic group having quaternary nitrogen atom, such as pyridinium, pyridazinium, pyrimidinium, pyrazinium or the like. And in the compound [I], M is always to be anionic charge when $R_3$ is heterocyclic group having quaternary nitrogen atom.

The objective cephalosporanic acid derivatives [I] may be prepared by reacting 7-amino-3-substituted methyl-3-cephem-4-carboxylic acids of the formula:

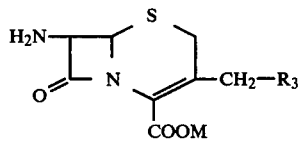

wherein $R_3$ and M are as defined above, or their derivatives at the amino group and/or their esters, with α-substituted glycine derivatives of the formula:

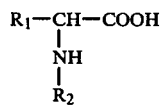

wherein $R_1$ and $R_2$ are as defined above, or their reactive derivatives at the carboxy group.

The derivative at the amino group of the compound [II] may be an acid addition salt, Schiff's base or the reaction product of the compound [II] and a silyl compound such as bis(trimethylsilyl)acetamide, or the like.

The reactive derivative at the carboxy group of the α-substituted glycine derivative [III] may be an acid halide, an acid anhydride, an activated amide, an activated ester, or the like. The suitable examples may be an acid chloride, an acid azide; a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid) or aromatic carboxylic acid (e.g. benzoic acid), or a symmetrical acid anhydride; an acid amide with imidazole, 4-substituted imidazole, dimethylpyrazole, triazole or tetrazole; or an ester (e.g. cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide or N-hydroxyphthalimide, 1-hydroxy-6-chloro-1H-benzotriazole), or the like. The suitable derivative can be optionally selected from them according to the kind of the α-substituted glycine derivative [III] to be used practically.

The reaction is usually carried out in a solvent such as water, acetone, dioxane, acetonitrile, chloroform, methylene chloride, ethylene chloride, tetrahydrofuran, ethyl acetate, N,N-dimethylformamide, pyridine or any other organic solvent inert to the reaction. Among these solvents, hydrophilic solvents may be used in a mixture with water.

When the α-substituted glycine derivative [III] is used in a form of the free acid or its salt in this reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methyl-imidazole), pentamethyleneketene-N cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-N-droxybenzisoxazolium salt, 2-ethyl-5-(m-sulfophenyl)isoxazolium hydroxide intramolecular salt, (chloromethylene)dimethylammonium chloride, and the like. The salt of the α-substituted glycine derivative [III] may be an alkali metal salt, an alkaline earth metal salt, an ammonium salt, a salt with an organic base such as triethylamine, dicyclohexylamine or the like.

The reaction may be carried out in the presence of a base such as alkali metal bicarbonate, trialkylamine, N-alkylmorphorine, N,N-dialkylbenzyl-amine, and the like. When the base or the condensing agent is in liquid, it can be used also as a solvent. The reaction temperature is not restrictive, and the reaction is usually carried out under cooling or at room temperature. Some of the objective compounds [I] of the formula:

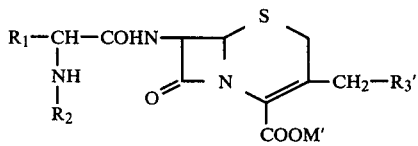

wherein
R₁ and R₂ are as defined above,
R'₃ is azido, aroylthio, in which the aryl moiety may be substituted with one to three lower alkoxy(s), heterocyclic-thio group, heterocyclic-carbonylthio group or heterocyclic-thiocarbonylthio group, in which the heterocyclic group (or moiety) may be substituted with lower alkyl, amino(lower)alkyl, in which the amino moiety may have a conventional protecting group or sulfo(lower)alkylamino(lower-)alkyl, provided that R₁ is hydrogen, lower alkyl or heterocyclic group when R₂ is phenoxy(lower)alkanoyl, in which the phenyl moiety have no substituent and R₃ is lower alkanoyloxy or lower alkyl substituted heterocyclic-thio group and
M' is hydrogen or nontoxic pharmaceutically acceptable cation, and their esters, may be prepared by reacting 7-(α-substituted glycinamido)-3-alkanoyloxymethyl-3-cephem-4-carboxylic acids of the formula:

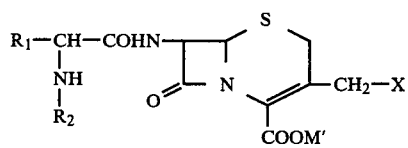

wherein R₁, R₂ and M' are as defined above, and X is lower alkanoyloxy, or their esters, with compounds [V] of the formula:

R'₃—H [V]

wherein R'₃ is as defined above, or their alkali metal salts or acid addition salts.

The term "lower alkanoyloxy" represented by X means the same as the alkanoyloxy group of R₃ mentioned above.

The alkali metal salts of the compound [V] may be a sodium salt, a potassium salt, or the like, and the acid addition salts may be hydrochloride, sulfate or the like.

The reaction of the 7-(α-substituted glycinamido)-3-alkanoyloxymethyl-3-cephem-4-carboxylic acid [IV] or their esters with the compound [V] or the alkali metal salts or acid addition salts thereof may be carried out in a solvent such as water, acetone, chloroform, nitrobenzene, dimethylformamide, methanol, ethanol, dimethylsulfoxide, or any other organic solvents inert to the reaction, preferably in a strongly polar solvent. Among the solvents, hydrophilic solvents may be used in a mixture with water. The reaction is preferably carried out in around neutral medium. When the compound [IV] or the compound [V] is used in a free form, the reaction is preferably conducted in the presence of a base such as alkali metal hydroxide, alkali metal carbonate, alkali metal bicarbonate, trialkylamine, and the like. The reaction temperature is not restrictive, and the reaction is usually carried out at room temperature or under warming. The reaction product can be isolated from the reaction mixture by conventional methods.

Further, some of the objective compound [I] of the formula:

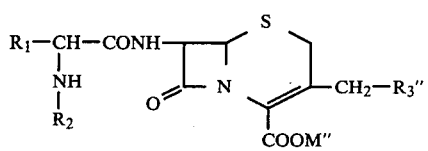

wherein
R₁ and R₂ are as defined above,
R"₃ is heterocyclic group having quaternary nitrogen atom and
M" is anionic charge, may be prepared by reacting 7-(α-substituted glycinamido)-3-alkanoyloxymethyl-3-cephem-4-carboxylic acids [IV] with six-membered aromatic heterocyclic compounds.

The term "six-membered aromatic heterocyclic compound" includes the compound which is able to form a quaternary nitrogen atom(ammonium ion), such as pyridine, pyridazine, pyrimidine, pyrazine or the like.

This reaction is usually carried out in water. When the reagent is in liquid, it can also be used as a solvent. Although the reaction temperature is not limited to a particular range, the reaction may be carried out usually at room temperature or under warming.

Furthermore, the objective compounds [I] may be also prepared by reacting cephalosporanic acid compounds of the formula:

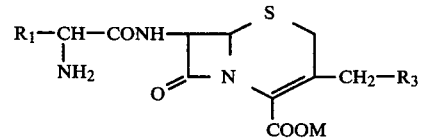

wherein R₁, R₃ and M are as defined above, or their derivatives at the amino group and/or their esters, with the carboxylic acids of the formula:

R₂—OH [VII]

wherein R₂ is as defined above, or their reactive derivatives.

The derivative at the amino group of the compound [VI] may be the same as that of the compound [II].

The reactive derivative of the compound [VII] may be the same as that of the α-substituted glycine derivative [III].

This reaction is carried out under similar reaction conditions (solvent, temperature and the like) to the first reaction of the compound [II] with the compound [III].

When the compounds [I] have the protected amino group, it may be removed in the course of the reaction or the post-treatment to give directly the objective compound [I] having a free amino group.

When the reaction product has the protected amino group, the amino protecting group may be removed from the reaction product, if desired, by applying a suitable removing reaction as mentioned below.

The removing reaction of the amino protecting group may be carried out by a conventional method such as elimination by acid, catalytic reduction, and the like, which is selected according to the kind of the protecting group on the amino group. The elimination by acid is one of the most suitable method and may be applied for the removal of the protecting group such as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, and the like. The acid applied to the above reaction is selected according to the kind of the amino protecting group, and the suitable acids are formic acid, trifluoroacetic acid, and the like, which can easily be distilled off under reduced pressure. When the elimination by acid is carried out in a solvent, a hydrophilic organic solvent, water or a mixture thereof is occasionally used as a solvent. The catalytic reduction may be applied for the removal of the amino protecting group such as benzyloxycarbonyl, substituted benzyloxycarbonyl, 2-pyridylmethoxycarbonyl, and the like. The suitable catalyst is palladium, and the other catalysts conventionally applied for the catalytic reduction may be also used. The trifluoroacetyl group may be removed by treating the reaction product with water, and the halogen-substituted alkoxycarbonyl group and 8-quinolyloxycarbonyl group may be removed by treating the reaction product with a heavy metal such as copper, zinc, and the like. The removing reaction of the amino protecting group may be carried out without isolation nor purification of the reaction product from the reaction medium.

All the reactants to be employed in the various processes of the present invention may be commercially available or be prepared by conventional methods well known to the art or by a variety of analogous methods applicable to production of such reactants. Some reactants in the present invention, for example, can be prepared by the following scheme:

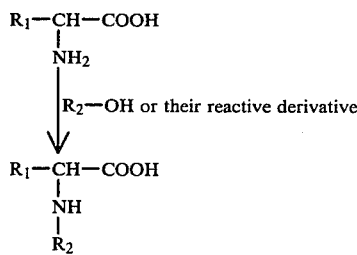

wherein $R_1$ and $R_2$ are as difined above.

In accordance with the present invention, a precipitate which forms during the reaction is separated from the reaction mixture by methods commonly used for this purpose, and the resulting reaction product may be subjected to routinely used purification procedures, for instance, to recrystallization from an appropriate solvent or a mixture of such solvents.

The compounds of the present invention exhibit a high antibacterial activity. For therapeutic administration the cephalosporin compounds according to the present invention are used in the form of pharmaceutical preparations which contain said compounds is admixture with a pharmaceutically acceptable organic or inorganic solid or liquid excipient suitable for oral or parenteral administration. The pharmaceutical preparations may be in solid form such as capsules, tablets, or dragees, or in liquid form such as solutions, or emulsions, or suppository. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 100 mg., 250 mg., and 500 mg. of the compounds according to the present invention has proved to be effective in treating diseases caused by bacterial infection. In general amounts between 10 mg. and about 1000 mg. of even more may be administered.

The following examples are given for the purpose of illustrating the present invention:

EXAMPLE 1

To a solution of 1.7 g of D-N-(2-nitrophenoxy)acetyl-2-phenylglycin and 550 mg of triethylamine in 50 ml of tetrahydrofuran, 600 mg of pivaloyl chloride were added at 5°–10° C. under stirring and stirring was continued for 30 minutes. To this solution, 50 ml of chloroform solution containing 1.4 g of 7-aminocephalosporanic acid and 600 mg of triethylamine at −10° C. under stirring, and stirring was continued for 1 hour at −10° C. and 4 hours at from 0° C. to room temperature. The reaction mixture was filtered and the filtrate was condensed under reduced pressure.

The condensed material was dissolved in 50 ml of water and the solution was adjusted to pH 7.0–7.5 by adding sodium hydrogencarbonate and washed with ethyl acetate. The aqueous solution was acidified by diluted hydrochloric acid and extracted twice by 50 ml of ethyl acetate. The extrace was washed with water, dried and condensed under reduced pressure. Residual material was washed with ether. 668 mg of powder of D-7-[N-(2-nitrophenoxy)acetyl-2-phenylglycinamido]-cephalosporanic acid, m.p. 203°–205° C. (decomp.), were obtained. Purified compound may be obtained by recrystallization from acetone.

Analysis: $C_{26}H_{24}O_{10}N_4S$. Calc. C 53.42, H 4.14, N 9.59, S 5.49. Found C 53.36, H 4.39, N 9.51, S 5.33.

U V Spectrum (95% $C_2H_5OH$).

λmax 260.5 mμ, E=205.8.

EXAMPLE 2

655 mg of N-DL-(2-nitrophenoxy)acetyl-2-phenylglycine were dissolved in 35 ml of tetrahydrofuran and stirred under ice cooling, and, 618 mg of dicyclohexylcarbodiimide were added and stirred for 30 minutes. To this solution, 35 ml of chloroform solution containing 550 mg of 7-amino-cephalosporaric acid and 606 mg of triethylamine were added under stirring at −10°--−13° C. and stirring was continued for 1 hour at the same temperature as above, 2 hours at 0° C., and further 3 hours at room temperature. The reaction mixture was filtered and filtrate was concentrated under reduced pressure. The concentrated residue was dissolved in 30 ml of water and the solution was adjusted to pH 7.5–8.0 by adding sodium hydrogencarbonate. After washing with ethyl acetate twice, the solution was adjusted to pH 3.5–4.0 by adding dilute sulfuric acid and extracted with ethyl acetate. The extract was washed with water and dried and ethyl acetate was distilled. The residue was washed with ether and dissolved in 95% ethanol and filtered. Ethanol was distilled off from the filtrate under reduced pressure. The resulted residue was washed with ether. 45 mg of powder of 7-[DL-N-(2- nitrophenoxy)acetyl-2-phenylglycinamido]cephalosporanic acid, m.p. 117°–125° C. (decomp.), were obtained.
U. V. Spectrum (95% $C_2H_5OH$).
λmax 261 mμ, E=157.7.

EXAMPLE 3

630 mg of N-(2-nitrophenyl)acetyl-2-phenylglycine were dissolved in 35 ml of tetrahydrofuran and stirred under ice cooling, and 618 mg of dicyclohexylcarbodiimide were added. To this solution, 35 ml of chloroform solution containing 544 mg of 7-aminocephalosporanic acid and 606 mg of triethylamine were added under stirring at −10°−−13° C.

The solution was stirred for 1 hour at the same temperature as above, 2 hours at 0° C. and further 3 hours at room temperature. The reaction mixture was filtered and the filtrate was concentrated under reduced pressure. The concentrated residue was dissolved in 30 ml of water and the solution was adjusted to pH 7.5–3.0. After washing with ethyl acetate twice, the solution was adjusted to pH 3.0–3.5 by adding dilute sulfuric acid and extracted with ethyl acetate. The extract was washed with water and dried and ethyl acetate was distilled. The residue was washed with ether. 267.7 mg of powder of 7-[N-(2-nitrophenyl)-acetyl-2-phenylglycinamido]cephalosporanic acid, m.p. 160°–170° C. (decomp.), were obtained.
U. V. Spectrum (95% $C_2H_5OH$).
λmax 259 mμ, E=167.8.

EXAMPLE 4

655 mg of N-(3-nitrophenoxy)acetyl-2-phenylglycine were dissolved in 35 ml of tetrahydrofuran and stirred under ice cooling, and 618 mg of dicyclohexylcarbodiimide were added and stirred for 30 minutes under ice cooling. To this solution, 35 ml of chloroform solution containing 550 mg of 7-aminocephalosporanic acid and 606 mg of triethylamine were added under stirring at −10°−−13° C.

The solution was stirred for 1 hour at the same temperature as above, 2 hours at 0° C. and further 3 hours at room temperature. The reaction solution was treated with same manner as described in Example 1. 226.1 mg of powder of 7-[N-(3-nitrophenoxy)acetyl-2-phenylglycinamido]cephalosporanic acid, m.p. 115°–122° C. (decomp.), were obtained.
U. V. Spectrum (95% $C_2H_5OH$).
λmax 265 mμ, E=216.2.

EXAMPLE 5

655 mg of N-(4-nitrophenoxy)acetyl-2-phenylglycine were dissolved in 35 ml of tetrahydrofuran and stirred under ice cooling, and 618 mg of dicyclohexylcarbodiimide were added and stirred for 30 minutes under ice cooling.
To this solution, 35 ml of chloroform solution containing 550 mg of 7-aminocephalosporanic acid and 606 mg of triethylamine were added under stirring at −10°−−13° C. The solution was stirred for 1 hour at the same temperature as above, for 2 hours at 0° C. and further 3 hours at room temperature.

The reaction solution was treated with same manner as described in Example 1. 137.4 mg of powder of 7-[N-(4-nitrophenoxy)acetyl-2-phenylglycinamido]cephalosporanic acid, m.p. 124°–128° C. (decomp.), were obtained.
U. V. Spectrum (95% $C_2H_5OH$).
λmax 290 mμ, E=201.2.

EXAMPLE 6

640 mg of N-(4-chlorophenoxy)acetyl-2-phenylglycine were dissolved in 35 ml of tetrahydrofuran and stirred under ice cooling, and 620 mg of dicyclohexylcarbodiimide were added and stirred for 30 minutes under ice cooling. To this solution, 35 ml of chloroform solution containing 550 mg of 7-aminocephalosporanic acid and 620 mg of triethylamine were added under stirring at −10°−−13° C.

The solution was stirred for 1 hour at the same temperature as above, 2 hours at 0° C. and further 3 hours at room temperature. The reaction solution was treated with same manner as described in Example 1, 52.1 mg of powder of 7-[N-(4-chlorophenoxy)acetyl-2-phenylglycinamido]cephalosporanic acid, m.p. 125°–130° C. (decomp.), were obtained.
U. V. Spectrum (95% $C_2H_5OH$).
λmax 265 mμ, E=158.

EXAMPLE 7

640 mg of N-(2-chlorophenoxy)acetyl-2-phenylglycine were dissolved in 35 ml of tetrahydrofuran and stirred under ice cooling, and 620 mg of dicyclohexylcarbodiimide were added and stirred for 30 minutes under ice cooling. To this solution, 35 ml of chloroform solution containing 550 mg of 7-aminocephalosporanic acid and 620 mg of triethylamine were added under stirring at −10°−−13° C. The solution was stirred for 1 hour at the same temperature as above, 2 hours at 0° C. and further 3 hours at room temperature. The reaction solution was treated with same manner as described in Example 1, 100.6 mg of powder of 7-[N-(2-chlorophenoxy)acetyl-2-phenylglycinamido]cephalosporanic acid, m.p. 128°–135° C. (decomp.), were obtained.
U. V. Spectrum (95% $C_2H_5OH$).
λmax 266 mμ, E=143.7.

EXAMPLE 8

3.7 g of D-N-(2,6-dichlorophenoxy)acetyl-2-phenylglycine and 1.2 g of triethylamine were dissolved in 70 ml of tetrahydrofuran and to this mixture, 1.2 g of pivaloyl chloride were added dropwise under stirring at 5°–10° C. The solution was stirred for 30 minutes at below −10° C., and 70 ml of chloroform solution containing 3.7 g of 7-aminocephalosporanic acid and 2.5 g of triethylamine were added dropwise at below −5° C. The solution was stirred for 1 hour at below −10° C., 1 hour at 0°–5° C. and further 3 hours at room temperature. Precipitates in the reaction mixture were filtered off and filtrate was concentrated under reduced pressure. To the concentrated residue, 50 ml of water were added and the solution was adjusted to pH 7.5–8.0 by adding sodium hydrogencarbonate. And then the solution was acidified by dilute hydrochloric acid, and extracted by ethyl acetate. The extract was washed with saturated sodium chloride solution and concentrated under reduced pressure. Concentrated residue was washed with ether. 4.15 g of powder of 7-[N-(2,6-dichlorophenoxy)acetyl-2-phenylglycinamido]cephalosporanic acid were obtained. Powdery purified substances melting at 167°–168° C. (decomp.) were obtained by recrystallization from aqueous acetone.
U. V. Spectrum (95% $C_2H_5OH$).
λmax 261.5 mμ, E=112.

EXAMPLE 9

710 mg of DL-N-(2,6-dichlorophenoxy)acetyl-2-phenylglycine and 210 mg of triethylamine were dissolved in 15 ml of tetrahydrofuran, and to this mixture, 240 mg of pivaloyl chloride were added under stirring on ice bath.

To this solution, 15 ml of chloroform solution containing 550 mg of 7-aminocephalosporanic acid and 210 mg of triethylamine were added dropwise at −17°−−20° C. and stirred for 30 minutes at −15°−−18° C., for 1 hour on ice bath and further 3 hours at room temperature. The reaction solution was concentrated under reduced pressure and concentrated residue was dissolved in 30 ml of water. The solution was adjusted to pH 7.5-8.0 by adding saturated solution of sodium hydrogencarbonate and washed with ethyl acetate. After acidified the solution by hydrochloric acid, extracted by ethyl acetate. The extract was washed with water, dried and concentrated under reduced pressure. The concentrated residue was washed with ether. 135.6 mg of powder of 7-[DL-N-(2,6-dichlorophenoxy)acetyl-2-phenylglycinamido]cephalosporanic acid, m.p. 140°-144° C. (decomp.), were obtained.

U. V. Spectrum (95% C$_2$H$_5$OH).
λmax 263.5 mμ, E=122.5.

EXAMPLE 10

600 mg of N-(2-nitrophenoxy)acetylvaline and 620 mg of dicyclohexylcarbodiimide were dissolved in 35 ml of anhydrous chloroform. To this solution, 35 ml of chloroform solution containing 550 mg of 7-aminocephalosporanic acid and 620 mg of triethylamine were added at −10°−−13° C. The solution was stirred for 1 hour at the same temperature as above, for 1 hour on ice bath and further 3 hours at room temperature. The reaction solution was treated with same manner as described in Example 1. 42 mg of powder of 7-[N-(2-nitrophenoxy)acetylvalinamido]cephalosporanic acid, m.p. 146°-151° C. (decomp.), were obtained.

U. V. Spectrum (95% C$_2$H$_5$OH).
λmax 261 mμ, E=200.9.

EXAMPLE 11

810 mg of N-(2-nitrophenoxy)acetylalanine and 330 mg of triethylamine were dissolved in 25 ml of anhydrous tetrahydrofuran, and to this solution 365 mg of pivaloyl chloride were added dropwise at 5°-10° C. The resulted solution containing mixed acid anhydride was stirred for 30 minutes at below −10° C. To this solution, 25 ml of anhydrous chloroform solution containing 820 mg of 7-aminocephalosporanic acid and 330 mg of triethylamine were added dropwise at below −5° C. The solution was stirred for 1 hour at below −10° C. and for 4 hours at from 0° C. to room temperature. The reaction solution was treated with same manner described in Example 1. 527.3 mg of powder of 7-[N-(2-nitrophenoxy)acetylalaninamido]cephalosporanic acid, m.p. 156°-174° C. (decomp.), were obtained.

U. V. Spectrum (C$_2$H$_5$OH).
λmax 261.5 mμ, E=196.2.

EXAMPLE 12

762 mg of N-(2-nitrophenoxy)acetylglycine and 350 mg of triethylamine were dissolved in 25 ml of anhydrous tetrahydrofuran, and to this solution 360 ml of pivaloyl chloride were added dropwise under stirring at 5°-10° C. The resulted solution containing mixed acid anhydride was stirred for 30 minutes at below −10° C. To this solution, 25 ml of aqueous chloroform solution containing 816 mg of 7-aminocephalosporanic acid and 350 mg of triethylamine were added dropwise at below −5° C. The solution was stirred for 1 hour at below −10° C. and 4 hours at from 0° C. to room temperature. The reaction solution was treated with the same manner as described in Example 1.

907 mg of powder of 7-[N-(2-nitrophenoxy)acetylglycinamido]cephalosporanic acid, m.p. 112°-117° C. (decomp.), were obtained.

U. V. Spectrum (95% C$_2$H$_5$OH).
λmax 259 mμ, E=200.6.

EXAMPLE 13

To a solution consisting of 503.7 mg of D-N-(4-chlorophenylthio)acetyl-2-phenylglycine, 151 mg of triethylamine and 10 ml of anhydrous tetrahydrafuran 180 mg of pivaloyl chloride were added dropwise. To this solution, a solution consisting of 408 mg of 7-aminocephalosporanic acid, 303 mg of triethylamine and 10 ml of anhydrous chloroform was added dropwise at below −5° C. and the solution was stirred for 40 minutes at below −10° C. and for 4.5 hours at room temperature. The reaction solution was concentrated under reduced pressure. Water was added to the residue and acidified by dilute hydrochloric acid, and then extracted by ethyl acetate. The extract was washed with water and dried, and concentrated under reduced pressure. The residue was pulverized with ether and precipitates were filtered. 322.5 mg of 7-[D-N-(4-chlorophenylthio)acetyl-2-phenylglycinamido]cephalosporanic acid, m.p. 142°-146° C. (decomp.), were obtained.

U. V. Spectrum (95% C$_2$H$_5$OH).
λmax 258.5 mμ, E=257.8.

EXAMPLE 14

To a solution consisting of 2.5 g of D-N-(2-nitrophenylthio)acetyl-2-phenylglycine, 0.85 g of triethylamine and 40 ml of anhydrous tetrahydrofuran, 1.26 g of pivaloyl chloride were added dropwise under stirring at 5°-10° C. and the solution was stirred for 30 minutes at below −10° C. To this solution, a solution consisting of 2.3 g of 7-aminocephalosporanic acid, 1.8 g of triethylamine and 40 ml of dried chloroform was added dropwise at below −5° C. The solution was stirred for 1 hour at −10°−−15° C. and 5 hours at room temperature. Ethyl acetate was added to the reaction solution and the solution was acidified by adding 10% hydrochloric acid. Ethyl acetate layer was separated, washed with water and dried, and then concentrated under reduced pressure.

The resulted residue was pulverzed with ether and precipitates were filtered. 1.88 g of 7-[D-N-(2-nitrophenylthio)acetyl-2-phenylglycinamido]cephalosporanic acid, m.p. 125°-127° C. (decomp.), were obtained.

U. V. Spectrum (95% C$_2$H$_5$OH).
λmax 246 mμ, E=308.5.

EXAMPLE 15

To 15 ml of anhydrous tetrahydrofuran solution containing 970 mg of D-N-(2-methoxyphenoxy)acetyl-2-phenylglycine and 304 mg of triethylamine, 362 mg of pivaloyl chloride were added dropwise at 5°-10° C. under stirring. After stirring for 30 minutes, 15 ml of anhydrous chloroform containing 820 mg of 7- aminocephalosporanic acid and 755 mg of triethylamine were added dropwise at below −5° C. to the above solution. This solution was stirred for 1.5 hours at −10°−−15° C. and 5 hours at from 0° C. to room temperature. The reaction solution was concentrated under reduced pressure and concentrated residue was dissolved in water. The solution was adjusted to pH 7.0–8.0 with sodium hydrogencarbonate aqueous solution and washed with ethyl acetate. Water layer was separated and adjusted to pH 4.0 with 10% hydrochloric acid and then extracted with ethyl acetate. The extract was washed with water dried over sodium sulfate and concentrated under reduced pressure. Concentrated residue was washed with ether. 220 mg of powder of 7-[D-N-(2-methoxyphenoxy)acetyl-2-phenyl-glycinamido]cephalosporanic acid, m.p. 130°–131° C. (decomp.), were obtained.

U. V. Spectrum (95% $C_2H_5OH$).
$\lambda$max 267 m$\mu$, E=150.5.

EXAMPLE 16

452 mg of pivaloyl chloride were added dropwise to 15 ml anhydrous tetrahydrofuran containing 950 mg of D-N-(3-methoxyphenoxy)acetyl-2-phenylglycine and 364 mg of triethylamine under stirring at 5°–10° C. The solution was stirred for 30 minutes at below −10° C., and to this solution, 15 ml of chloroform solution containing 980 mg of 7-aminocephalosporanic acid and 760 mg of triethylamine were added dropwise at below −5° C. The solution was stirred for 1.5 hours at −10°−−15° C. and 4 hours at from 0° C. to room temperature. The reaction solution was treated with the same manner as described in Example 15. to give 345 mg of powder of 7-[D-N-(3-methoxyphenoxy)acetyl-2-phenyl-glycinamido]cephalosporanic acid, m.p. 125°–127° C. (decomp.), were obtained.

U. V. Spectrum (95% $C_2H_5OH$).
$\lambda$max 268 m$\mu$, E=150.

EXAMPLE 17

362 mg of pivaloyl chloride were added dropwise to 15 ml of anhydrous tetrahydrofuran containing 870 mg of D-N-(2,6-dimethoxyphenoxy)acetyl-2-phenylglycine and 304 mg of triethylamine under stirring at 5°–10° C. and the solution was stirred for 30 minutes at below −10° C. To this solution, 15 ml of chloroform solution containing 820 mg of 7-aminocephalosporanic acid and 635 mg of triethylamine were added dropwise at below −5° C. This solution was stirred for 1 hour at −10°−−15° C. and 5 hours at from 0° C. to room temperature. The reaction solution was concentrated under reduced pressure and concentrated residue was dissolved in water and adjusted to pH 7.0–8.0 by adding sodium hydrogencarbonate and the solution was washed with ethyl acetate. Water layer was separated and adjusted to pH 2.0 with dilute hydrochloric acid and extracted with ethyl acetate. Extract was washed with water, dried over sodium sulfate and concentrated under reduced pressure, concentrated residue was washed with ether. 450 mg of powder of 7-[D-N-(2,6-dimethoxyphenoxy)-acetyl-2-phenylglycinamido]cephalosporanic acid, m.p. 97°–105° C. (decomp.), were obtained.

U.V. Spectrum (95% $C_2H_5OH$).
$\lambda$max 256 m$\mu$, E=146.5.
$\lambda$max 270 m$\mu$, E=129.

EXAMPLE 18

725 mg of pivaloyl chloride were added dropwise to 20 ml of anhydrous tetrahydrofuran solution containing 1540 mg of N-(2-nitrophenoxy)acetyl-2-(2-thienyl)glycine and 605 mg of triethylamine at −5°−−10° C. and the solution was stirred for 30 minutes at below −10° C. To this solution, 20 ml of anhydrous chloroform solution containing 1650 mg of 7-aminocephalosporanic acid and 1270 mg of triethylamine were added dropwise at below −5° C. This solution was stirred for 1.5 hours at −10°−−15° C. and for 4 hours at from 0° C. to room temperature. The reaction solution was concentrated under reduced pressure and concentrated residue was dissolved in water. The resulted solution was adjusted to pH 7.0–8.0 by adding sodium hydrogencarbonate, washed with ethyl acetate. Water layer was separated, adjusted to pH 2.0 by dilute hydrochloric acid and extracted by ethyl acetate. The extract was washed with water, dried over sodium sulfate and concentrated under reduced pressure. Concentrated residue was washed with ether. 1090 mg of powder of 7-[N-(2-nitrophenoxy)-acetyl-2-(2-thienyl)glycinamido]cephalosporanic acid was obtained. When recrystallized 500 mg of the above substance from acetone, 100 mg of purified crystals, m.p. 187°–189° C. (decomp.), were obtained.

U.V. Spectrum (20% tetrahydrofuran).
$\lambda$max 235 m$\mu$, E=301.
$\lambda$max 270 m$\mu$, E=195.

EXAMPLE 19

725 mg of pivaloyl chloride were added dropwise to 30 ml of anhydrous tetrahydrofuran containing 1830 mg of D-N-(2-nitro-4-chlorophenoxy)acetyl-2-phenylglycine and 605 mg of triethylamine under stirring at 5°–10° C. and the solution was stirred for 30 minutes at below −10° C. To this solution, 30 ml of anhydrous chloroform solution containing 1640 mg of 7-aminocephalosporanic acid and 1260 mg of triethylamine were added dropwise at below −5° C. This solution was stirred for 1.5 hours at −10°−−15° C. and 4 hours at from 0° C. to room temperature. The reaction solution was treated with same manner as described in Example 15. 1160 mg of powder of 7-[D-N-(2-nitro-4-chlorophenoxy)-acetyl-2-phenylglycinamido]cephalosporanic acid were obtained. When recrystallized 500 mg of the above substance from aqueous acetone, purified substance having m.p. 165°–168° C. (decomp.), was obtained.

U.V. Spectrum (20% tetrahydrofuran).
$\lambda$max 279.5 m$\mu$, E=339.

EXAMPLE 20

434 mg of pivaloyl chloride were added dropwise to 15 ml of anhydrous tetrahydrofuran solution containing 1040 mg of D-N-(2-tert-butylphenoxy)acetyl-2-phenylglycine and 361 mg of triethylamine under stirring at 5°–10° C. After stirring the solution for 30 minutes, 15 ml of anhydrous chloroform solution containing 980 mg of 7-aminocephalosporanic acid and 755 mg of triethylamine were added dropwise at below −5° C. The solution was stirred for 1.5 hours at −10°−−15° C. and for 4 hours at from 0° C. to room temperature. The reaction solution was concentrated under reduced pressure, and concentrated residue was dissolved in water. The solution was adjusted to pH 7.0–8.0 by adding sodium hydrogen carbonate aqueous solution and washed with ethyl acetate. Water layer was separated, adjusted to pH 4.0 by hydrochloric acid and extracted with ethyl acetate. The extract was washed, dried over sodium sulfate and ethyl acetate was distilled off under reduced pressure. The residue was washed with a mixture of ether and petroleum ether. 810 mg of powder of D-7-[N-(2-tert-butylphenoxy)acetyl-2-phenyl-glycinamido]cephalosporanic acid were obtained. To acetone solution containing 600 mg of the above substance, 180 mg of dicyclohexylamine were added and resulted precipitates were filtered. 300 mg of powder of dicyclohexylamine salt of D-7-[N-(2-tert-butylphenoxy-2-phenylglycinamido]cephalosporanic acid were obtained. m.p. 177°–178° C. (decomp.).

Analysis: $C_{30}H_{33}N_3O_8S \cdot C_{12}H_{23} N \cdot 2H_2O$: Calcd. C 62.06, H 7.44, N 6.89, S 3.94. Found C 62.24, H 7.12, N 6.74, S 3.98.

U.V. Spectrum (95% $C_2H_5OH$).
$\lambda$max 268 m$\mu$, E=113.

EXAMPLE 21

3.6 g of N-(3-trifluoromethylphenoxy)acetyl-2-(2-thienyl)glycine and 3.2 g of 7-aminocephalosporanic acid were added to 30 ml of anhydrous tetrahydrofuran and the solution was cooled to 5° C. To this solution, 1.4 g of pivaloyl chloride were added under stirring, and stirring was continued further for 30 minutes. After cooling to −5° C., to this solution, 30 ml of anhydrous chloroform solution dissolved 3.0 g of 7-aminocephalosporanic acid and 2.2 g of triethylamine were added dropwise under cooling to below −5° C. This solution was stirred for 15 hours at below −5° C. and then 3.5 hours at room temperature. Precipitates were filtered off from the reaction solution and filtrate was concentrated under reduced pressure. To the residue, water and ethyl acetate were added and acidified by dilute hydrochloric acid and extracted by ethyl acetate. The extract was washed with water, dried and concentrated under reduced pressure. Produced crystals in the concentrated solution were filtered. 575 mg of crystals of 7-[N-(3-trifluoromethylphenoxy)acetyl-2-(2-thienyl)-glycinamido]cephalosporanic acid, m.p. 148°–151° C. (decomp.), were obtained.

U.V. Spectrum (95% $C_2H_5OH$).
$\lambda$max 220 m$\mu$, E=256.7.
$\lambda$max 240 m$\mu$, E=213.
$\lambda$inf 268 m$\mu$, E=142.6.

EXAMPLE 22

The process of Example 21 was repeated using 3.0 g of N-(2-nitro-4-chlorophenoxy)acetyl-2-(2-thienyl)glycine and 2.7 g of 7-aminocephalosporanic acid. 577 mg of crystals of 7-[N-(2-nitro-4-chlorophenoxy)acetyl-2-(2-thienyl)glycinamido]cephalosporanic acid, m.p. 150°–155° C., were obtained.

U.V. Spectrum (20% tetrahydrofuran).
$\lambda$inf 240 m$\mu$, E=311.4.
$\lambda$inf 263 m$\mu$, E=188.

EXAMPLE 23

The process of Example 21 was repeated using 3.6 g of N-(2,6-dichlorophenoxy)acetyl-2-(2-thienyl)glycine and 3.2 g of 7-aminocephalosporanic acid. 1.35 g of crystals of 7-[N-(2,6-dichlorophenoxy)acetyl-2-(2-thienyl)glycinamido]cephalosporanic acid were obtained. m.p. 150°–155° C. (decomp.).

U.V. Spectrum (pH 6.4 phosphoric acid buffer solution).
$\lambda$inf 220 m$\mu$, E=296.2.

$\lambda$inf 236 m$\mu$, E=224.
$\lambda$inf 265 m$\mu$, E=134.

EXAMPLE 24

0.7 g of pivaloyl chloride was added dropwise to a solutionconsisting of 1.5 g of D-N-(2,6-xylyloxy)acetyl-2-phenylglycine, 0.7 g of tirethylamine and 30 ml of dried tetrahydrofuran at −5° C. The solution was stirred for 30 minutes at the same temperature as above. To this solution, 30 ml of dried chloroform solution containing 1.5 g of 7-aminocephalosporanic acid and 1.0 g of triethylamine were added at a stroke at below −10° C. This solution was stirred for 1 hour at the same temperature as above and then 3 hours at room temperature. The reaction solution was filtered and the filtrate was concentrated under reduced pressure, and water was added to the resulted residue. The solution was acidified by diluted hydrochloric acid, extracted with ethyl acetate and the extract was washed with water and dried, and concentrated under pressure. The residue was pulverized with ether and precipitates were filtered 1.011 g of 7-[D-N-(2,6-xylyloxy)acetyl-2-phenylglycinamido]cephaslosporanic acid, m.p. 120°–130° C. (decomp.), were obtained.

U.V. Spectrum (20% tetrahydrofuran)
$\lambda$max 260 m$\mu$, E=157.1.

EXAMPLE 25

550 mg of N-phenylacetyl-2-phenylglycine was dissolved in 15 ml of tetrahydrofuran and this solution was stirred under ice cooling. To this solution, 610 mg of dicyclohexylcarbodiimide were added and stirred for 30 minutes under ice cooling. To this solution, 15 ml of chloroform solution containing 542 mg of 7-aminocephalosporanic acid and 606 mg of triethylamine were added under stirring at −10°−−13° C. The solution was stirred for 1 hour at the same temperature as above, for 2 hours at 0° C. and further for 3 hours at room temperature. The reaction solution was filtered and filtrate was concentrated under reduced pressure, concentrated residue was dissolved in 30 ml of water and adjusted to pH 7.5–8.0 by sodium hydrogencarbonate. After washing twice with ethyl acetate, the solution was adjusted to pH 3.0–3.5 by dilute sulfuric acid and extracted with ethyl acetate. The extract was washed with water, dried and ethyl acetate was distilled off. The residue was washed with ether. 55.7 mg of powder of 7-(N-phenylacetyl-2-phenylglycinamido)cephalosporanic acid, m.p. 120°–128° C. (decomp.), were obtained.

U.V. Spectrum (95% $C_2H_5OH$).
$\lambda$max 253 m$\mu$, E=175.

EXAMPLE 26

3.0 g of DL-N-(3-phenylpropionyl)-2-(2-thienyl)glycine and 1.2 g of triethylamine were dissolved in 30 ml of dried tetrahydrofuran. To this solution, 1.4 g. of pivaloyl chloride were added and stirred for 30 minutes. To this solution, 30 ml of chloroform containing 3.0 g of 7-aminocephalosporanic acid and 2.2 g of triethylamine were added dropwise at −5° C. This solution was stirred for 1.5 hours at below −5° C. and for 3.5 hours at room temperature. The reaction solution was concentrated under reduced pressure. Water and ethyl acetate were added to the produced residue and acidified by adding dilute hydrochloric acid. Ethyl acetate layer was separated and washed by water, dried and concentrated under reduced pressure. Precipitates in the concentrated solution were filtered. 1.5 g of 7-{N-3(-phenylpropionyl)-2-(2-thienyl)-DL-glycinamido}cephalosporanic acid, m.p. 166°–168° C. (decomp.), were obtained.

U.V. Spectrum (95% $C_2H_5OH$).
$\lambda$max 240 m$\mu$, E=260.
$\lambda$inf 270 m$\mu$, E=132.

EXAMPLE 27

To a solution of 6.0 g of D-N-(2-nitro-4-chlorophenylacetyl)-2-phenylglycine, 1.74 g of dried triethylamine and 50 ml of tetrahydrofuran, a solution of 2.07 g of pivaloyl chloride and 50 ml of tetrahydrofuran was added dropwise over a period of 7 minutes at −5° C. After completion of adding, the solution was stirred for 30 minutes at the same temperature as above. This solution was added at a stroke at −25° C. to a solution of 6.2 g of 7-amino-3-(1-methyl-1H-tetrazol-5-yl)thiomethyl-3-cephem-4-carboxylic acid, 2.88 g of triethylamine, 15 ml of acetone and 15 ml of water. After removing the cooling bath, the mixed solution was stirred for 1.5 hours at room temperature. Tetrahydrofuran and acetone were distilled off from the reaction solution. To the residue, water and ethyl acetate were added and adjusted to pH 2 by adding dilute hydrochloric acid. After removing precipitates, ethyl acetate layer was separated, washed with water and then dried on magnesium sulfate. Ethyl acetate was distilled off and the residue was dissolved in acetone. Precipitates were filtered and filtrate was treated with active carbon and then acetone was distilled off. Ether was added to the residue and stirred ove night, and precipitate was filtered. 1.49 g powder of 7-[D-N-(2-nitro-4-chlorophenylacetyl)-2-phenylglycinamide]-3-(1-methyl-1H-tetrazol-5-yl)thiomethyl-3-cephem-4-carboxylic acid. m.p. 173° C. (decomp.) were obtained.

N.M.R. spectrum: $\delta$(DMSO-$d_6$)ppm: 3.67 (2H, broad s), 3.95 (3H, s) 4.08 (2H, d), 4.33 (2H, s), 5.05 (1H, d), 5.67 (2H, m), 7.02–8.13 (8H, m).

EXAMPLE 28

To a solution of 2.0 g of D-N-(2-nitro-4-chlorophenylacetyl)-2-phenylglycine, 0.58 g of triethylamine and 20 ml of tetrahydrofuran, a solution of 0.69 g of pivaloyl chloride and 4 ml of tetrahydrofuran was added over a period of 5 minutes at 0°−−5° C. and the solution was stirred for 30 minutes at the same temperature. To this solution, a solution of 1.98 g of 7-amino-3-(5-methyl-1,3,4-thiadiasol-2-yl)thiomethyl-3-cephem-4-carboxylic acid, 0.82 g of triethylamine, 10 ml of acetone and 10 ml of water was added at a stroke at −10° C. This mixed solution was stirred vigorously for 30 minutes at −5°−−9° C. and then for 1 hour at room temperature. Precipitates in the reaction solution were filtered off, and acetone and tetrahydrofuran were distilled off under reduced pressure. To the residue, sodium hydrogencarbonate aqueous solution was added under ice cooling and precipitates were filtered. The precipitates were dissolved in water and ethyl acetate was added to this solution and adjusted to pH 2 by dilute hydrochloric acid. After separating ethyl acetate layer and ethyl acetate was distilled off under reduced pressure. The residue was washed with ether. 0.2 g of 7-[D-N-(2-nitro-4-chlorophenylacetyl)-2-phenylglycinamido]-3-(5-methyl-1,3,4-thiadiazol-2-yl)thiomethyl-3-cephem-4-carboxylic acid. m.p. 169° C. (decomp.) were obtained.

N.M.R. spectrum: $\delta$(DMSO-$d_6$)ppm: 2.67 (3H, s), 3.67 (2H, broad s), 4.02 (2H, s), 4.37 (2H, d), 5.10 (1H, d), 5.63 (2H, m) 7.2–8.06 (8 H, m)

EXAMPLE 29

753 mg of N-phenoxyacetylvaline and 930 mg of dicyclohexylcarbodiimide were dissolved in 35 ml of anhydrous tetrahydrofuran. To this solution, 35 ml of anhydrous chloroform solution containing 316 mg of 7-aminocephalosporanic acid and 909 mg of triethylamine were added at −10°−−13° C. The solution was stirred for 1 hour at the same temperature as the above, 2 hours on ice bath and further 3 hours at room temperature. Precipitates in the reaction solution were filtered off and filtrate was concentrated. The residue was dissolved in 30 ml of water and the solution was adjusted to pH 7.5–8.0 by adding sodium hydrogen carbonate saturated aqueous solution and then washed with ethyl acetate. Water layer was separated and acidified by hydrochloric acid and then extracted with ethyl acetate. The extract was washed with water and dried and ethyl acetate was distilled off. The residue was washed with ether. 73 mg of powder of 7-(N-phenoxyacetylvalinamido)cephalosporanic acid, m.p. 112°–115° C. (decomp.), were obtained.

U.V. spectrum (95% $C_2H_5OH$).
$\lambda$max 266 m$\mu$, E=165.3.

EXAMPLE 30

670 mg of N-phenoxyacetylalanine and 930 mg of dicyclohexylcarbodiimide were dissolved in 35 ml of anhydrous tetrahydrofuran. To this solution, 35 ml of anhydrous chloroform solution obtaining 820 mg of 7-aminocephalosporanic acid and 930 mg of triethylamine were added at −10°−−13° C. The solution was stirred for 1 hour at the same temperature as the above, 2 hours on ice bath and further 3 hours at room temperature. The reaction solution was treated with the same as Example 1. 331.2 mg of powder of 7-(N-phenoxyacetylalaninamido)cephalosporanic acid, m.p. 105°–110° C. (decomp.), were obtained.

U.V. spectrum (95% $C_2H_5OH$).
$\lambda$max 264 m$\mu$, E=127.6.
$\lambda$max 275.5 m$\mu$, E=112.2.

EXAMPLE 31

3.0 g of N-phenoxyacetyl-2-(2-thienyl)glycine and 1.2 g of triethylamine were dissolved in 30 ml of anhydrous tetrahydrofuran and cooled to 5° C. To this solution, 1.4 g of pivaloyl chloride were added dropwise under stirring for 30 minutes. To this reaction solution, a solution of 3.0 g of 7-aminocephalosporanic acid and 2.2 g of triethylamine in 30 ml of anhydrous chloroform was added dropwise under cooling at below −5° C. This mixed solution was stirred for 15 hours at −5° C. and 3.5 hours at room temperature. Precipitates were filtered off from the reaction solution and the filtrate was concentrated under reduced pressure. To the residue, water and ethyl acetate were added and acidified by adding dilute hydrochloric acid and extracted with ethyl acetate. The ethyl acetate extract was washed with water, dried and concentrated under reduced pressure. Crystals produced in the concentrated solution were filtered. 1.186 g of 7-[N-(phenoxyacetyl-2-(2-thienyl)glycinamido]cephalosporanic acid, m.p. 150°–155° C. (decomp.) were obtained.

U.V. spectrum (20% tetrahydrofuran)
λmax 240 mμ, E=272.9.
λinf 268 mμ, E=180.5.
λinf 275 mμ, E=143.

EXAMPLE 32

The following compounds were obtained in a similar manner to those of Examples 1 to 31.

(1) 7-[D-N-(2-carboxyphenylthioacetyl)-2-phenylglycinamido]-3-(5-methyl-1,3,4-thiadiazol-2-yl)thiomethyl-3-cephem-4-carboxylic acid,
m.p. 198° to 200.5° C., (decomp.).
I.R. Spectrum: $\nu^{Nujol}$(cm$^{-1}$): 1775, 1720, 1698, 1662, 1640.

(2) Pivaloyloxymethyl ester of 7-[D-N-(4-chloro-2-nitrophenoxyacetyl)-2-phenylglycinamido]cephalosporanic acid,
m.p. 148° to 150° C.

(3) Disodium salt of 7-[N-(2-nitro-4-chlorophenoxy)acetyl-2-phenyl-D-glycinamido]-3-(5-sulfomethylaminomethyl-1,3,4-thiadiazol-2-yl)thiomethyl-3-cephem-4-carboxylic acid,
m.p. above 250° C.
$\nu^{Nujol}$(cm$^{-1}$): 1758

(4) Methyl ester of D-7-[N-(2-nitrophenoxy)acetyl-2-phenylglycinamido]cephalosporanic acid.
N.M.R. Spectrum: $\delta^{DMSO-d6}$(ppm): 2.0(3H,s), 3.5(2H,broads), 3.8(3H,s), 4.6, 5.05(2H,AB-q), 4.85(2H,s), 5.05(1H,d), 5.75(2H,m), 7.0–8.0(9H,m).

(5) 4-Methoxybenzyl ester of D-7-[N-(2-nitrophenoxy)acetyl-2-phenylglycinamido]cephalosporanic acid.
N.M.R. Spectrum: $\delta^{DMSO-d6}$(ppm): 1.95(3H,s), 3.5(2H,broads), 3.75(3H,s), 4.6, 4.95(2H,AB-q), 4.8(2H,s), 5.05(1H,d), 5.15 (2H,s), 5.75(2H,m), 6.8–8.0(13H,m).

EXAMPLE 33

0.5 g of 7-[D-N-(2-nitrophenoxy)acetyl-2-phenylglycinamido]cephalosporanic acid was dissolved in 4 ml of pyridine and 6 ml of water added. This solution was heated to 60° C. for 6 hours and then the reaction solution was concentrated under reduced pressure and precipitates were filtered off. The filtrated was washed with ethyl acetate and concentrated. The concentrated residue was washed with acetone. 50 mg of 1-[4-carboxy-7-{D-N-(2-nitrophenoxy)acetyl-2-phenylglycinamido}-3-cephem-3-ylmethyl]-pyridinium-hydroxide inner salt, m.p. 200° C. (decomp.), were obtained.

U.V. spectrum (20% tetrahydrofuran).
λmax 260.5 mμ, E=160.

EXAMPLE 34

1.2 g of 7-[D-N-(2-nitrophenoxy)acetyl-2-phenylglycinamido]cephalosporanic acid, 330 mg of sodium 2-thiophenthiocarboxylate and 170 mg of sodium hydrogencarbonate were dissolved in 50 ml of a pH 6.4 phosphoric acid buffer solution and stirred for 6.5 hrs. at 60° C. To the reaction solution was added 10% hydrochloric acid to make acidic, and then the reaction solution was extracted twice with 50 ml of ethyl acetate. The extract solution was washed with water, dried, and then concentrated under reduced preduced pressure. To the concentrate was added ether, filtered and dried.

There obtained 1.08 g of a crystalline powder 7-[D-N-(2-nitrophenoxy)acetyl-2-phenylglycinamido]-3-(2-thienylcarbonylthiomethyl)-3-cephem-4-carboxylic acid, mp. 105°–113° C. (decomp.).

U.V. spectrum (20% tetrahydrofuran).
λmax 264 mμ, E=210.1.
λinf 300 mμ, E=150.1.

EXAMPLE 35

To 50 ml of a pH 6.9 phosphate buffer were added 2.0 g of 7-[D-N-(2-nitrophenoxy)acetyl-2-phenylglycinamido]cephalosporanic acid and 0.6 g of sodium thiobenzoate and further added acetone to dissolve an insoluble material while warming at 60° C. The mixture was heated for 6.5 hrs. at the same temperature. The reaction mixture was cooled to room temperature and a precipitate was separated by filtration. It was dissolved in aqueous acetone and acetone was distilled off. The aqueous layer was acidified with a dilute hydrochloric acid and a precipitate was filtered to obtain sodium 7-[D-N-(2-nitrophenoxy)acety-2-phenylglycinamido]-3-benzoylthiomethyl-3-cephem-4-carboxylate, mp. 180° C. (decomp.).

Analysis: $C_{31}H_{26}N_4O_9S_2$: Calcd. C 56.20, H 3.93, N 8.46. Found C 56.45, H 4.01, N 8.12.

U.V. spectrum (20% tetrahydrofuran sol.).
λmax 272.5 mμ, E=282.

EXAMPLE 36

500 mg of 7-[D-N-(2-nitrophenoxy)acetyl-2-phenylglycinamido]cephalosporanic acid and 120 mg of 5-methyl-1,3,4-oxadiazol-2-thiol were dissolved in 30 ml of a pH 6.5 borate buffer and stirred for 6 hrs. at 60° C. The reaction solution was washed twice with ether. To the separated aqueous layer was added a dilute hydrochloric acid to make pH 4.0 and the solution was extracted with ethyl acetate. The extract was washed, dried and distilled under reduced pressure to remove the solvent. By washing the residue, there was obtained 300 mg of powder-like 7-[D-N-(2-nitrophenoxy)acetyl-2-phenylglycinamido]-3-(5-methyl-1,3,4-oxadiazol-2-yl)thiomethyl-3-cephem-4-carboxylic acid, mp. 115°–120° C.

U.V. spectrum (pH 6.4 phosphate buffer).
λ max 257 mμ, E=227.

EXAMPLE 37

To 18 ml of a pH 5.0 phosphate buffer were added 1170 mg of 7-[D-N-(2-nitrophenyl)acetyl-2-phenylglycinamido]cephalosporanic acid, 274 mg of 1-methyl-1H-tetrazol-5-thiol and 369 mg of sodium hydrogen carbonate and the mixture was stirred for 5.5 hrs. at 60° C. The reaction mixture was treated in the way similar to that of Example 36 and the resulting powder was converted into the salt with dicyclohexylamine. It was a powder-like dicyclohexylamine salt of 7-[D-N-(2-nitrophenoxy)acetyl-2-phenylglycinamido]-3-(1-methyl-1-H-tetrazol-5-yl)thiomethyl-3-cephem-4-carboxylic acid (890 mg), mp. 178°–179° C. (decomp.). It was recrystallized from aqueous acetone to obtain 240 mg of the white crystaline pure product.

U.V. spectrum (95% C$_2$H$_5$OH).
λ max 260 mμ, E=149.

EXAMPLE 38

To 40 ml of a pH 5.8 phosphate buffer were added 730 mg of 7-[D-N-(2-nitrophenoxy)acetyl-2-phenylglycinamido]cepharosporanic acid, 150 mg of 5-methyl-1,3,4-thiadiazol-2-thiol and 231 mg of sodium hydrogen carbonate and the mixture was stirred for 5.5 hrs. at 60° C. The reaction mixture was treated in the way similar to that of Example 36 and resulting powder was converted into a salt with dicyclohexylamine. It was a powderlike dicyclohexylamine salt of 7-[D-N-(2-nitrophenoxy)acetyl-2-phenylglycinamido]-3-(5-methyl-1,3,4-thiadiazole-2-yl)thiomethyl-3-cephem-4-carboxylic acid (604 mg), mp. 192°–193° C. (decomp.). It was recrystallized from aqueous tetrahydrofuran to obtain 200 mg of the white crystalline pure product.

U.V. spectrum (95% C$_2$H$_5$OH).
λ max 260 mμ, E=140.5.

EXAMPLE 39

To 40 ml of a pH 6.1 phosphate buffer was added 1.1 g of 7-[D-N-(2-nitrophenoxy)acetyl-2-phenylglycinamido]cepharosporanic acid and 0.26 g of 5-methyl-4H-1,2,4-triazole-3-thiol and the mixture was stirred for 5 hrs. at 60° C. The reaction mixture was filtered on a cellulose powder and the filtrate was washed with ethyl acetate. To the separated aqueous layer was added a dilute hydrochloric acid to make pH 2.0 and the solution was extracted with ethyl acetate. The extract was washed with a 50% sodium chloride aqueous solution dried and distilled under reduced pressure to remove the solvent. The residue after washing with water was suspended in water. It was extracted with ethyl acetate. The extract was washed with water, dried and distilled under reduced pressure to remove the solvent, whereby a powder-like 7-[D-N-(2-nitrophenoxy)acetyl-2-phenylglycinamido]-3-(5-methyl-4H-1,2,4-triazol-3-yl)thiomethyl-3-cephem-4-carboxylic acid (0.1 g), mp. 154° C. (decomp.) was obtained.

U.V. spectrum (pH 6.4 phosphate buffer).
λ max 268.5 mμ, E=203.

EXAMPLE 40

To 30 ml of a pH 6.1 phosphate buffer were added 650 mg of 7-[D-N-(2-nitrophenoxy)acetyl-2-phenylglycinamido]cephalosporanic acid and 130 mg of 1,3,4-thiadiazol-2-thiol and further added a small quantity of sodium bicarbonate, and the mixture was stirred for 8.5 hrs. while warming at 60° C. To the reaction mixture was added a dilute hydrochloric acid to make pH 4.0 and the solution was washed with ether. To the separated aqueous layer was added a dilute hyrochloric acid to make pH 2.0 and was filtered to obtain a crystalline precipitate. After the precipitate was washed with 99% ethanol, it was dissoved in 10 ml of a mixture of ethyl acetate and acetic acid (20:1), and was separated by column chromatography on silica-gel using a mixture of ethyl acetate and acetic acid (10:1) as developing solvent. The third fraction of each 10 ml of the effluents was concentrated to obtain a powder-like 7-[D-N-(2-nitrophenoxy)acetyl-2-phenylglycinamido]-3-(1,3,4-thiadiazol-2-yl)thiomethyl-3-cephem-4-carboxylic acid, mp. 135° C. (decomp.).

U.V. spectrum (pH 6.4 phosphate buffer).
λ max 269.5 mμ, E=216.

EXAMPLE 41

To 20 ml of a pH 6.5 phosphate buffer were added 0.5 g of 7-[D-N-(2,6-dichlorophenoxy)acetyl-2-phenylglycinamido]cephalosporanic acid and 150 mg of potassium thiobenzoic acid and added acetone while warming at 60° C. to dissolve an impurity. And the mixture was heated for 6.5 hrs. The reaction mixture was left overnight and filtered to obtain a precipitate. The precipitate was recrystallized from 99% ethanol to obtain a crystal of 7-[D-N-(2,6-dichlorophenoxy)acetyl-2-phenylglycinamide]-3-benzoylthiomethyl-3-cephem-4-carboxylic acid (250 mg), mp. 173° C. (decomp.).

U.V. spectrum (30% tetrahydrofuran sol.).
λ max 240 mμ, E=190.
λ max 276 mμ, E=210.

EXAMPLE 42

To 30 ml of a pH 7.0 phosphate buffer were added 500 mg of 7-[D-N-(2,6-dichlorophenoxy)acetyl-2-phenylglycinamido]cephalosporanic acid and 100 mg of 1-methyl-1H-tetrazole-5-thiol and warmed at 60° C. for 6 hrs. To the reaction mixture was added a dilute hydrochloric acid to make pH 4.0 and was extracted with ethyl acetate and the ethyl acetate layer was concentrated. To the residue was added ether and filtered to obtain a precipitate. The precipitate was dissolved in an acetone. The solution was concentrated and to the residue was added an ethyl acetate to filter off a precipitate. To the filtrate was added ether and filtered to obtain a powder-like 7-[D-N-(2,6-dichlorophenoxy)acetyl-2-phenylglycylamido]-3-(1-methyl-1H-tetrazol-5-yl)thiomethyl-3-cephem-4-carboxylic acid (50 mg), mp. 135°–140° C. (decomp.).

U.V. spectrum (pH 6.4 phosphate buffer).
λ max 265 mμ, E=128.

EXAMPLE 43

To 20 ml of a pH 7.12 phosphate buffer were added 500 mg of 7-[D-N-(2,6-dichlorophenoxy)acetyl-2-phenylglycinamido]cephalosporanic acid and 120 mg of 5-methyl-1,3,4-thiadiazole-2-thiol and warmed at 60° C. for 4 hrs. The reaction mixture was treated in the same way as Example 36 to obtain a powder-like 7-[D-N-(2,6-dichlorophenoxy)acetyl-2-phenylglycinamido]-3-(5-methyl-1,3,4-thiadiazol-2-yl)thiomethyl-3-cephem-4-carboxylic acid (200 mg).

U.V. spectrum (pH 6.4 phosphate buffer).
λ max 271 mμ, E=159.

EXAMPLE 44

A mixture comprising 2 g of 7-[D-N-(2-nitrophenoxy)acetyl-2-(2-thionyl)glycinamido]cephalosporanic acid, 330 mg of sodium bicarbonate, 30 ml of a pH 6.4 phosphate buffer and 765 mg of 4-methylpiperazine-1-dithiocarboxylic acid was stirred for 6 hrs. at 60° C. To the reaction mixture was added hydrochloric acid to make acidic, and after adding ethylacetate, the mixture was filtered to obtain a precipitated crystal. The crystal was dissolved in aqueous acetone and was filtered off an insoluble matter. The filtrate was concentrated under the reduced pressure and filtered to obtain a crystal of 7-[D-N-(2-nitrophenoxy)acetyl-2-(2-thienyl)-glycinamido]-3-84-methyl-1-piperazinyl)thiocarbonylthiomethyl-3-cephem-4-carboxylic acid (1.6 g), mp. 157°–160° C. (decomp.).

U.V. spectrum (20% tetrahydrofuran sol.).

λ max 269 mμ, E=260.8.

EXAMPLE 45

To 20 ml of a pH 6.5 phosphate buffer were added 500 mg of 7-[DL-N-(2-nitrophenoxy)acetyl-2-(2-thionyl)glycinamido]cephalosporanic acid, 140 mg of 1-methyl-1H-tetrazole-2-thiol and 195 mg of sodium bicarbonate and the mixture was stirred for 6 hrs. at 60° C. To the reaction mixture was sodium hydrogen carbonate to make pH 7.0 and washed with ether. The aqueous layer was washed ethyl acetate. To the aqueous layer was added a dilute hydrochloric acid to make pH 4.0 and the mixture was extracted with ethyl acetate. The extract was washed with water and after being dried with sodium sulfate, it was filtered off ethyl acetate under the reduced pressure. The residue was washed with ether to obtain 361 mg of powder-like 7-[DL-N-(2-nitrophenoxy)acetyl-2-(2-thienyl)-glycinamido]-3-(1-methyl-1H-tetrazol-5-yl)thiomethyl-3-cephem-4-carboxylic acid.

To 3 ml of an acetone solution containing 361 mg of the product was added 3 ml of an acetone solution containing 110 mg of a dicyclohexylamine. After the mixture was allowed to stand, a crystal was filtered to obtain 57 mg of a dicyclohexylamine salt of 7-[DL-N-(2-nitrophenoxy)acetyl-2-(2-thienyl)glycinamido]-3-(1-methyl-1H-tetrazol-5-yl)thiomethyl-3-cephem-4-carboxylic acid, mp. 175°-176° C. (decomp.).

U.V. spectrum (95% $C_2H_5OH$).

λ max 235 mμ, E=290.
λ max 270 mμ, E=145.

EXAMPLE 46

2 g of 7-[DL-N-(2-nitrophenoxy)acetyl-2-(2-thienyl)-glycinamido]cephalosporanic acid, 450 mg of 5-methyl-1,3,4-thiadiazole-2-thiol and 571 mg of sodium hydrogen carbonate were dissolved in 25 ml of a pH 6.4 phosphate buffer and the mixture was stirred for 6 hrs. at about 60° C. After the mixture was allowed to stand for cooling, the reaction mixture was made acidic with hydrochloric acid and extracted with ethyl acetate. The extract was washed with water, dried and then concentrated under reduced pressure. The concentrate was washed with ether to obtain 1.2 g of powder-like 7-[DL-N-(2-nitrophenoxy)acetyl-2-(2-thienyl)glycinamido]-3-(5-methyl-1,3,4-thiadiazol-2-yl)thiomethyl-3-cephem-4-carboxylic acid. 450 mg of the product was recrystallized from aqueous acetone to obtain 290 mg of the pure product of mp. 131°-135° C. (decomp.).

Analysis: $C_{25}H_{22}N_6O_8S_4$: Calcd. C 45.31, H 3.35, N 12.68, S 19.35. Found C 45.61, H 3.42, N 12.63, S 19.63.

U.V. spectrum (20% tetrahydrofuran).

λ max 269 mμ, E=247.3.

EXAMPLE 47

A solution comprising 1.77 g of 7-[DL-N-(2-nitrophenoxy)acetyl-2-(2-thienyl)glycinamido]cephalosporanic acid, 550 mg of sodium hydrogen carbonate, 30 ml of a pH 6.4 phosphate buffer and 450 mg of a benzimidazole-2-thiol was stirred for 6 hrs. at 60° C. After the mixture was allowed to stand for cooling, it was filtered to obtain a crystal. After the crystal was suspended in water, to the suspension was added hydrochloric acid and was washed with an ethyl acetate. The insoluble material obtained by filtration was dissolved in aqueous acetone. After the insoluble material was filtered off, the filtrate was concentrated and the resulting crystal was filtered to obtain 7-[DL-N-(2-nitrophenoxy)acetyl-2-(2-thienyl)glycinamido]-3-(2-benzimidazelyl)thiomethyl-3-cephem-4-carboxylic acid (927 mg), mp. 155°-160° C. (decomp.).

U.V. spectrum (20% tetrahydrofuran).

λ max 274 mμ, E=224.6.
λ max 282 mμ, E=222.
λ max 291 mμ, E=201.2.
λ inf 268 mμ, E=220.4.

EXAMPLE 48

To 20 ml of a pH 6.5 phosphate buffer were added 600 mg of 7-[D-N-(2-nitro-4-chlorophenoxy)acetyl-2-phenylglycinamido]cephalosporanic acid, 124 mg of 1-methyl-1H-tetrazol-5-thiol and 101 mg of sodium hydrogen carbonate and the mixture was stirred for 7 hrs. at 60° C. To the reaction mixture was added dilute hydrochloric acid to make acidic and then added ether. The separated precipitate was filtered and to it was added acetone. The mixture was concentrated under reduced pressure. To the residue was added ether and the separated precipitate was dissolved in pH 7.0-8.0 sodium hydrogen carbonate aqueous solution and was washed with ethyl acetate. To the separated aqueous layer was added a dilute hydrochloric acid to make pH 4.0 and the mixture was extracted with ethyl acetate. After the extract was washed with water and dried, the solvent was filtered off under reduced pressure. To the residue was added an ether and filtered to obtain a powder-like 7-[D-N-(2-nitro-4-chlorophenoxy)acetyl-2-phenylglycinamido]-3-(1-methyl-1H-tetrazol-5-yl)thiomethyl-3-cephem-4-carboxylic acid (195 mg), mp. 163°-170° C. (decomp.).

U.V. spectrum (pH 6.4 phosphate buffer).

λ max 267 mμ, E=177.4.

EXAMPLE 49

A mixture of 3.6 g of 7-[D-N-(2-phenoxycarbonyl-phenoxyacetyl)-2-phenylglycinamido]cephalosporanic acid, 1.06 g of sodium hydrogen carbonate, 656 mg of 1-methyl-1H-tetrazole-5-thiol, 108 ml of water and 54 ml of acetone was stirred for 8 hrs. at 65°-70° C. To the reaction mixture was added water to make the total 300 ml and treated with an active carbon. The reaction solution was made pH 2.0 with 10% hydrochloric acid under cooling and extracted twice with ethyl acetate. After the extract was washed twice with a saturated aqueous solution of sodium chloride, it was dried over magnesium sulfate. The solution was filtered off its ethyl acetate under reduced pressure and filtered to obtain a separated cryatal. After the crystal was washed with 5 ml of ethyl acetate, it was dried to obtain 0.77 g of 7-[D-N-(2-phenoxycarbonylphenoxyacetyl)-2-phenylglycinamido]-3-(1-methyl-1H-tetrazol-5-yl)thiomethyl-3-cephem-4-carboxylic acid, mp. 169°-171° C. (decomp.).

N.M.R. spectrum: $\delta(DMSO-d_6)_{ppm}$: 3.61 (2H, broad s), 3.94 (3H, s), 4.30 (2H, q, J=18 Hz), 4.79 (2H, s), 5.00 (1H, d, J=5 Hz), 5.80 (2H, m), 6.94-8.20 (14H, m).

EXAMPLE 50

A Mixture of 3.5 g of 7-[N-(2-nitro-4-chlorophenoxyacetyl)-2-phenyl-D-glycinamido]cephalosporanic acid, 1.04 g of 5-aminomethyl-1,3,4-thiadiazol-2-thiol hydrochloride, 1.43 g of sodium bicarbonate, 100 ml of pH 5.2 phosphate buffer solution and 30 ml of acetone was dissolved into a solution under warming at 60° to 65° C. The resultant solution was adjusted to pH 5.2 with 5% hydrochloric acid, and then stirred at 60° to 65° C. for 7 hours. The appearing precipitates were filtered, while warming, washed with hot water and hot acetone and then dried to give 2.2 g of 7-[N-(2-nitro-4-chlorophenoxyacetyl)-2-phenyl-D-glycinamido]-3-85-aminomethyl-1,3,4-thiadiazol-2-yl)thio methyl-3-cephem-4-carboxylic acid, m.p. 180° to 185° C. The product was dissolved in acidic methanol with warming at 40° to 50° C. and insoluble substances were filtered off. To the filtrate was added water and aqueous ammonia is adjust it to pH 3 to 4, and the appearing precipitates were collected by filtration to give the pure product, m.p. 185° C.

EXAMPLE 51

(1) 3.1 g of 7-[N-(2-nitro-4-chlorophenoxyacetyl)-2-phenyl-D-glycinamido]cephalosporanic acid, 1.23 g of 1-(2-t-butoxycarbonyl aminoethyl)-1H-tetrazol-5-thiol and 0.84 g of sodium bicarbonate were dissolved in a mixture of 100 ml of pH 6.4 phosphate buffer solution and 50 ml of acetone at 60° to 65° Cl and the resultant solution was stirred for 18 hours at the same temperature. After removal of acetone from the reaction mixture under reduced pressure, the residue was added with 100 ml of water, and extracted was with 100 ml of ethyl acetate four times. The extract was washed with 5% aqueous hydrochloric acid and water in turn and dried and the solvent was added with ether and triturated to give powder (2.4 g.) of 7-[N-(2-nitro-4-chlorophenoxyacetyl)-2-phenyl-D-glycinamido]-3-[1-(2-t-butoxycarbonylaminoethyl)-1H-tetrazol-5-yl]thiomethyl-3-cephem-4-carboxylic acid, m.p. 200° C. (dec.).

I.R. Spectrum: $\nu^{Nujol}$(cm$^{-1}$): 1778.

(2) 2.0 g of thus obtained 7-[N-(2-nitro-4-chlorophenoxyacetyl)-2-phenyl-D-glycinamido]-3-[1-(2-t-butoxycarbonylaminoethyl)-1H-tetrazole-5-yl]thiomethyl-3-cephem-4-carboxylic acid was dissolved in 10 ml of formic acid and stirred at room temperature for 3 hours. Formic acid was removed from the resultant mixture under reduced pressure and water was added to the residue. The appearing precipitates were filtered, washed with methanol and dried to give crude product (1.6 g.) of 7-[N-(2-nitro-4-chlorophenoxyacetyl)-2-phenyl-D-glycinamido]-3-[1-(2-aminoethyl)-1H-tetrazol-5-yl]thiomethyl-3-cephem-4-carboxylic acid. 1.4 g of the product was dissolved in 4 ml of acetic acid and 20 ml of methanol was added thereto with stirring at room temperature. The appearing precipitates were collected by filtration, washed with methanol and ether in turn and dried to give the pure product (1.0 g.), m.p. 175° C. (dec.).

I.R. Spectrum: $\nu^{Nujol}$(cm$^{-1}$): 1768.

EXAMPLE 52

A mixture of 3.1 g of 7-[D-N-(4-chloro-2-nitrophenoxyacetyl)-2-phenylglycinamido]cephelosporanic acid, 1.5 g of potassium salt of 3,4,5-trimethoxybenzoic S-acid, 45 ml of phosphate buffer solution (pH 6.9) and 35 ml of acetone was stirred at 60° to 63° C. for 9.5 hours. The resultant solution was cooled to room temperature. The appearing precipitates were collected by filtration, suspended in 10% hydrochloric acid and extracted with ethyl acetate. The ethyl acetate layer was washed twice with water, dried over magnesium sulfate and then concentrated under reduced pressure. The residue was triturated with ether and the powder was purified by chromatography on silica gel with a mixture of ethyl acetate and acetone to give 0.45 g of 7-[D-N-(4-chloro-2-nitrophenoxyacetyl)-2-phenyl-glycinamido]-3-(3,4,5-trimethoxybenzoyl)thiomethyl-3-cephem-4-carboxylic acid, m.p. 167° to 170° C. (decomp.).

EXAMPLE 53

A solution consisting 1.7 g of 7-[D-N-(2-nitrophenoxy) acetyl-2-(2-thienyl)-glycinamido]cephalosporanic acid, 550 mg of sodium hydrogencarbonate, 440 mg of sodium azide, 30 ml of phosphoric acid butter solution of pH 6.4 and a small amount of sodium acetate was stirred for 6 hours at 60° C. The reaction solution was acidified by hydrochloric acid, extracted with ethyl acetate and ethyl acetate was distilled under reduced pressure. 1.32 g of 7-[D-N-(2-nitrophenoxy)-acetyl-2-(2-thienyl)glycinamido]-3-azidomethyl-3-cephem-4-carboxylic acid, m.p. 100°-108° C. (decomp.) were obtained.

U.V. spectrum (20% tetrahydrofuran).

$\lambda$ inf 263 m$\mu$, E=197.15.

EXAMPLE 54

4.0 g of 7-(D-2-phenylglycinamido)cephalosporanic acid and 2.52 g of sodium hydrogen carbonate were dissolved in a mixed solution of 20 ml of acetone and 40 ml of water. To this solution, 20 ml of dried acetone solution containing 2.60 g of (2-nitrophenoxy)acetyl chloride were added dropwise under ice-cooling and stirring over a period of 10 minutes, and the mixture was stirred for 1 hour at the same temperature as above and for 2.5 hours at room temperature. Acetone was distilled off from the reaction mixture under reduced pressure, and the residue was washed twice with 250 ml of ethyl acetate. Water layer was acidified by adding 10% hydrochloric acid and extracted twice with 250 ml of ethyl acetate. Ethyl acetate extract was dried over magnesium sulfate and concentrated.

Crystals produced were filtered. 4.60 g of 7-[D-N-(2-nitrophenoxy)acetyl-2-phenylglycinamido]cephalosporanic acid were obtained. Purified compound, m.p. 200°-201° C. (decomp.) was obtained by recrystallisation from 40% aqueous acetone.

U.V. spectrum (pH 6.4 phosphoric acid buffer solution).

$\lambda$ max 264 m$\mu$, E=224.

Analysis: $C_{26}H_{24}N_4O_{10}S$: Calcd. C 53.42, H 4.14, N 9.57, S 5.49. Found C 53.87, H 4.12, N 9.48, S 5.48.

EXAMPLE 55

3.47 g of 7-(D-2-phenylglycinamido)-3-methyl-3-cephem-4-carboxylic acid and 2.52 g of sodium hydrogen carbonate were dissolved in a mixed solution of 20 ml of acetone and 40 ml of water. To this solution, 20 ml of dried acetone solution containing 2.60 g of (2-nitrophenoxy)acetyl chloride were added dropwise under ice-cooling and stirring over a period of 10 minutes, and the mixture was stirred for 1 hour at the same temperature as above and for 3 hours at room temperature. Acetone was distilled off from the reaction mixture under reduced pressure, and the residue was washed with ethyl acetate. Water layer was acidified by adding 10% hydrochloric acid and extracted with 500 ml of ethyl acetate. Ethyl acetate extract was dried over magnesium sulfate and concentrated. Crystals produced were filtered. 4.73 g of 7-[D-N-(2-nitrophenoxy)acetyl-2-phenylglycinamido]-3-methyl-3-cephem-4-carboxylic acid were obtained. Purified crystals of pale yellowish needle, m.p. 178°-180° C. (decomp.) were obtained by recrystallization from 70% aqueous acetone.

Analysis: $C_{24}H_{22}N_4O_8S$: Calcd. C 54.75, H 4.21, N 10.64, S 6.09. Found C 54.39, H 4.19, N 10.37, S 5.93.

EXAMPLE 56

To a solution consisting of 2.5 g of 7-[DL-2-(2-thienyl)glycinamido]-3-(5-methyl-1,3,4-thiadiazol-2-yl)thiomethyl-3-cephem-4-carboxylic acid, 820 mg of sodium hydrogencarbonate, 25 ml of water and 10 ml of acetone, 10 ml of acetone solution containing (2-nitrophenoxy)acetyl chloride were added dropwise under ice-cooling and stirring. The mixture was stirred for 1 hour under ice-cooling and for 3 hours at room temperature. The reaction solution was washed with ethyl acetate, acidified with dilute hydrochloric acid and extracted.

The extract was washed with water, dried and concentrated under reduced pressure. The residue was pulverized with ether and filtered. 1 g of 7-[DL-N-(2-nitrophenoxy)acetyl-2-(2-thienyl)glycinamido]-3-(5-methyl-1,3,4-thiadiazol-2-yl)thiomethyl-3-cephem-4-carboxylic acid was obtained. By recrystallization from aqueous acetone, purified compound, m.p. 131°-135° C. (decomp.) was obtained.

U.V. spectrum (20% tetrahydrofuran).
$\lambda$max 269 m$\mu$, E=247.

EXAMPLE 57

To a solution consisting of 4 g of 7-(D-2-phenylglycinamido)cephalosporanic acid, 2.52 g of sodium hydrogen carbonate, 40 ml of water and 20 ml of acetone, 20 ml of dried acetone solution containing 2.7 g of (2-t-butylphenoxy)acetyl chloride were added dropwise over a period of 10 minutes under ice-cooling and the mixture was stirred for 1 hour at the same temperature as above and then for 3 hours at room temperature. Acetone was distilled off from the reaction solution under reduced pressure. The residue was washed with 300 ml of ethyl acetate and adjusted to pH 2 with 10% hydrochloric acid and extracted with ethyl acetate. The extract was dried over magnesium sulfate, treated with active carbon and ethyl acetate was distilled off under reduced pressure. The residue was crystallized with petroleum ether. 3.0 g of pale yellowish powdery crystals 7-[D-N-(2-t-butylphenoxy)acetyl-2-phenylglycinamido]cephalosparanic acid were obtained. Dicyclohexylamine salt of the above compound m.p. 177°-178° C. (decomp.) was obtained by treating the compound with dicyclohexylamine by a conventional method.

U. V. spectrum (95% $C_2H_5OH$).
$\lambda$max 268 m$\mu$, E=113.

EXAMPLE 58

To a solution consisting of 800 mg of 7-(D-2-phenylglycinamido)-3-methyl-3-cephem-4-carboxylic acid, 400 mg of sodium hydrogen carbonate, 8 ml of water and 4 ml of acetone, 1.5 ml of acetone solution containing (2-t-butylphenoxy)acetylchloride [prepared from 500 mg of (2-t-butylphenoxy)acetic acid and thionyl chloride] were added dropwise under ice-cooling, while maintaining pH of the solution to 7.5-8.0. The solution was stirred for 1 hour at the same temperature as above and then for 2 hours at room temperature. Acetone was distilled off from the reaction solution under reduced pressure. Residual solution was acidified by dilute hydrochloric acid and extracted 3 times with 30 ml of ethyl acetate. The extract was washed with water, dried over magnesium sulfate and concentrated under reduced pressure. The residue was pulverized with petroleum ether. 633 mg of 7-[D-N-(2-t-butylphenoxy)acetyl-2-phenylglycinamido]-3-methyl-3-cephem-4-carboxylic acid were obtained.

U. V. spectrum (pH 6.4 phosphoric acid buffer solution).
$\lambda$max 264 m$\mu$, E=141.

EXAMPLE 59

To a solution consisting of 3.47 g of 7-(D-2-phenylglycinamido)-3-methyl-3-cephem-4-carboxylic acid, 2.52 g of sodium hydrogen carbonate, 40 ml of water and 20 ml of acetone, 20 ml of dried acetone solution containing 2.36 g of (2,6-xylyloxy)acetyl chloride were added dropwise over a period of 10-15 minutes under ice-cooling and stirring. The solution was stirred for 1 hour at the same temperature as above and then for 3 hours at room temperature. Acetone was distilled off from the reaction solution under reduced pressure and the residue was washed twice with 300 ml of ethyl acetate. Water layer was acidified by 10% hydrochloric acid and extracted with 500 ml of ethyl acetate. The extract solution was dried on magnesium sulfate and concentrated under reduced pressure. 3.78 g of yellowish powdery crystals 7-[D-N-(2,6-xylyloxy)acetyl-2-phenylglycinamido]-3-methyl-3-cephem-4-carboxylic acid were obtained.

U.V. spectrum (pH 6.4 phosphoric acid buffer solution).
$\lambda$max 263 m$\mu$, E=149.

EXAMPLE 60

6.3 g of 7-(D-phenylglycinamido)-3-(5-methyl-1,3,4-thiadiazol-2-yl)thiomethyl-3-cephem-4-carboxylic acid were suspended in 63 ml of chloroform. To this suspension medium, 4.85 g of triethylamine were added little by little at 5° C. and the mixture was made uniform solution. To this solution, 2-nitro-4-chlorophenylacetic acid chloride which was prepared from 3.12 g of 2-nitro-4-chlorophenylacetic acid, 20 ml of benzene, 2.2 ml of thionyl chloride and 1 drop of dimethylformamide by conventional method, was added dropwise under stirring at 2°-4° C. over a period of 40 minutes. The mixture was stirred for 2 hours at the same temperature as above and then 6 hours at room temperature. Chloroform was distilled off from the reaction solution under reduced pressure. The produced jelly residue was added to a mixed solution of acetone and water (1:1), and dilute sodium hydrogen carbonate aqueous solution was added to the mixture. The mixed solution was acidified to pH 4.6 by adding dilute hydrochloric acid and precipitates were filtered. Methanol was added to the precipitates and insoluble materials were filtered off and the filtrate was concentrated under reduced pressure to dryness. Ethyl acetate was added to the produced residue and insoluble materials (1.3 g) were filtered. Filtrate was washed with water and concentrated under reduced pressure to dryness. The produced residue was washed with ether. 0.5 g of white powder of 7-{D-N-(2-nitro-4-chlorophenylacetyl)-2-phenylglycinamido)-3-(5-methyl-1,3,4-thiadiazol-2-yl)thiomethyl-3-cephem-4-carboxylic acid was obtained. 1.3 g of above mentioned insoluble materials in ethyl acetate were dissolved in aqueous solution of sodium hydrogen carbonate and treated by the same method as described above, 0.33 g of the object compound was obtained. 0.83 g of the object compound was obtained in total. this compound was washed with a mixed solution of ethyl acetate and ether (1:2 v/v) to give 740 mg of purified compound m.p. 169° C. (decomp.)

N.M.R. spectrum: δ(DMSO-d$_6$) ppm: 2.67 (3H, s), 3.67 (2H, broad s), 4.02 (2H, s), 4.37 (2H, d), 5.10 (1H, d), 5.63 (2H, m), 7.2-8.06 (8H, m).

EXAMPLE 61

A mixture of 5.04 g of 2-(2-phenoxycarbonylphenoxy)acetic acid, 20 ml of thionyl chloride, 20 ml of benzene and 1 drop of dimethylformamide was refluxed for 2 hours. Excess amount of thionyl chloride and benzene was distilled off from the above mixture, and residue was dissolved in 50 ml of anhydrous acetone. This solution was added dropwise into a mixture consisting of 5 g of 7-(D-2-phenylglycinamido)cephalosporanic acid, 3.32 g of sodium hydrogen carbonate, 150 ml of water and 25 ml of acetone, under ice-cooling and stirring over a period of 40 minutes. The mixed solution was stirred for 1 hour at the same temperature as above and then water was added until the solution becomes to 500 ml. Insoluble materials were filtered and the filtrate was adjusted to pH 2 by 10% hydrochloric acid under cooling, and extracted twice with ethyl acetate. The extract was washed twice with saturated aqueous solution of sodium chloride and dried over magnesium sulfate and then concentrated to 50 ml under reduced pressure. Precipitates produced in the concentrated solution were filtered and washed with ethyl acetate. 4.0 g of colorless crystal of 7-[D-N-{2-(2-phenoxycarbonylphenoxy)acetyl}-2-phenylglycinamido]cephalosporanic acid, m.p. 188° C. (decomp.) were obtained.

N.M.R. spectrum: δ(DMSO-d$_6$) ppm: 2.07 (3H, s), 3.53 (2H, broad s), 4.83 (2H, s), 4.90 (2H, q, J=12 Hz), 5.07 (1H, d, J=5 Hz), 5.53-6.10 (2H, m), 7.10-8.33 (9H, m).

EXAMPLE 62

A mixture consisting of 5.13 g of 2-(2-nitro-4-chlorophenoxy)acetic acid, 20 ml of thionyl chloride, 20 ml of benzene and 1 drop of dimethylformamide were refluxed for 2 hours. Excess amount of thionyl chloride and benzene from the above mixture, and residue was dissolved in 50 ml of anhydrous acetone. This solution was added dropwise into a mixture consisting of 7 g of 7-(D-2-phenylglycinamido)-3-methyl-3-cephem-4-carboxylic acid, 5.09 g of sodium hydrogen carbonate, 100 ml of water and 50 ml of acetone under ice-cooling and stirring over a period of 30 minutes. This mixture was stirred for 1 hour on an ice-bath and then for 3 hours at room temperature. The reaction solution was added into 1 l of water and washed twice with ethyl acetate. Water layer was adjusted to pH 2.5 by 10% hydrochloric acid under cooling, and extracted twice with ethyl acetate. The extract was washed with water, dried over magnesium sulfate and then concentrated under reduced pressure. Crystals produced were filtered. 6.5 g of light yellowish crystals, m.p. 187° C. (decomp.), 7-[D-N-{2-(2-nitro-4-chlorophenoxy)acetyl}-2-phenylglycinamido]-3-methyl-3-cephem-4-carboxylic acid were obtained.

N.M.R. spectrum: δ(DMSO-d$_6$) ppm: 2.03 (3H, s), 3.38 (2H, q, J=18 Hz), 4.90 (2H, s), 4.99 (1H, d, J=5 Hz), 5.55-5.82 (2H, m), 7.26-8.06 (8H, m).

EXAMPLE 63

Acetone solution of 2-(2,4-dichloro-6-sulfophenoxy)acetic acid chloride was added dropwise into a mixture consisting of 3.75 g of 7-(D-2-phenylglycinamido)cephalosporanic acid, 1.58 g of sodium hydrogen carbonate, 50 ml of water and 50 ml of acetone under stirring at 0°-5° C. During the reaction, the solution was adjusted to pH 7-8 by adding aqueous solution of sodium hydrogen carbonate. After completion of adding, the solution was stirred for 2 hours at 0°-5° C., and insoluble materials were filtered off and acetone was distilled off from the filtrate. Adding ethyl acetate to the residual water layer, the solution was acidified by 10% hydrochloric acid, and shaked. Crystals produced was filtered and washed with ethyl acetate. 2.7 g of crude crystals of 7-[D-N-{2-(2,4-dichloro-6-sulfophenoxy)acetyl}-2-phenylglycinamido]cephalosporanic acid were obtained. According to suspending 2.53 g of the above crude crystals in 50 ml of acetone and stirring for 1 hour and filtering them, 22 g of purified compound were obtained.

I.R. spectrum: ν$_{max}$$^{Nujor}$ cm$^{-1}$: 1782, 1750, 1710, 1665.

N.M.R. spectrum: δ(DMSO-d$_6$) ppm: 2.00 (3H, s), 3.50 (2H, broad s), 4.72, 4.89 (2H, ABq, J=14 Hz), 4.80 (2H, s), 5.00 (1H, d, J=4.5 Hz), 5.7 (2H, m), 7.2-7.7 (7H, m).

What we claim is:

1. Compounds of the formula:

$$R_1-\underset{\underset{R_2}{\overset{|}{NH}}}{\overset{|}{C}}HCOHN-\overset{S}{\underset{COOM}{\underset{|}{\text{cephem}}}}-CH_2-R_3$$

wherein
R$_1$ is phenyl or thienyl,
R$_2$ is phenoxy(lower)alkanoyl, in which the phenyl moiety may be substituted with one or two halogen atoms or a nitro group,
R$_3$ is azido, benzoylthio in which the phenyl moiety may be substituted with one to three lower alkoxy(s), thenoylthio or piperazinyl-thiocarbonyl-thio group, in which the piperazinyl group may be substituted with lower alkyl, and
M is hydrogen or a nontoxic, pharmaceutically acceptable cation.

2. Compounds according to claim 1, wherein
R$_1$ is phenyl, and
R$_3$ is benzoylthio, in which phenyl moiety may be substituted with one to three lower alkoxy(s), or thenoylthio.

3. Compounds according to claim 1, wherein
R$_1$ is thienyl,
R$_2$ is phenoxy(lower)alkanoyl, in which phenyl moiety may be substituted with a nitro group,
R$_3$ is azido, or piperazinyl-thiocarbonyl-thio group, in which the piperazinyl group may be substituted with lower alkyl, and
M is hydrogen or a nontoxic, pharmaceutically acceptable cation.

4. A compound according to claim 2, wherein
R$_1$ is phenyl,
R$_2$ is 2-nitrophenoxyacetyl,
R$_3$ is benzoylthio,
M is hydrogen or sodium cation.

5. A compound according to claim 2, wherein
R$_1$ is phenyl,
R$_2$ is 2-nitrophenoxyacetyl, $R_3$ is 2-thenoylthio,
M is hydrogen.
6. A compound according to claim 2, wherein
$R_1$ is phenyl,
$R_2$ is 2,6-dichlorophenoxyacetyl,
$R_3$ is benzoylthio,
M is hydrogen.
7. A compound according to claim 2, wherein
$R_1$ is phenyl,
$R_2$ is 4-chloro-2-nitrophenoxyacetyl,
$R_3$ is 3,4,5-trimethoxybenzoylthio,
M is hydrogen.
8. A compound according to claim 3, wherein
$R_1$ is thienyl,
$R_2$ is 2-nitrophenoxyacetyl,
$R_3$ is 4-methyl-piperazin-1-ylthiocarbonylthio,
M is hydrogen
9. A compound according to claim 3, wherein
$R_1$ is thienyl,
$R_2$ is 2-nitrophenoxyacetyl,
$R_3$ is azido,
M is hydrogen.

* * * * *